Figure 1:
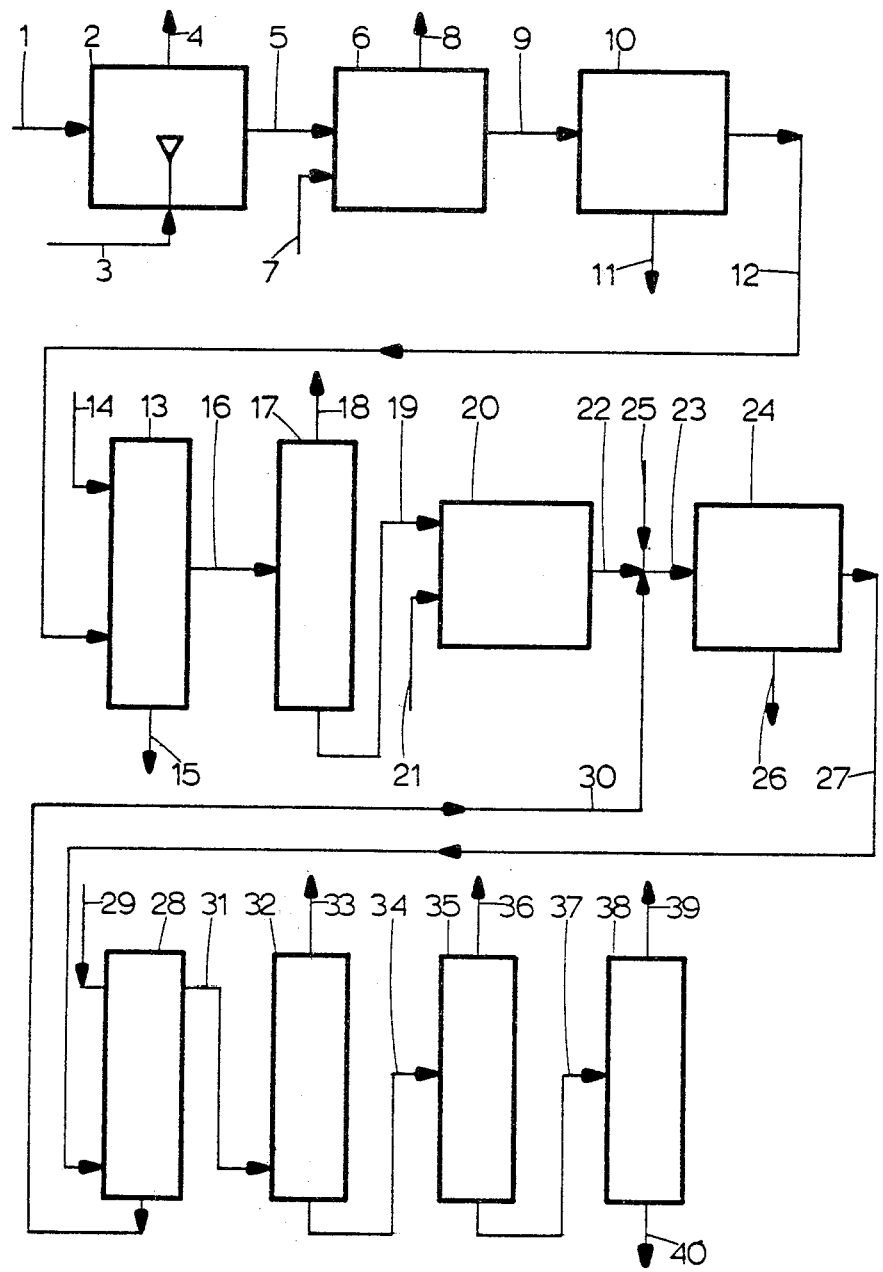

United States Patent [19]  [11] 4,326,085
De Cooker  [45] Apr. 20, 1982

[54] PROCESS FOR REMOVING ALKALI METAL CARBOXYLATES FROM MIXTURES CONTAINING A CYCLOAKANONE AND A CYCLOALKANOL OBTAINED IN OXIDATION OF CYCLOALKANES

[75] Inventor: Mario G. R. T. De Cooker, Sittard, Netherlands

[73] Assignee: Stamicarbon B.V., Geleen, Netherlands

[21] Appl. No.: 158,578

[22] Filed: Jun. 11, 1980

[30] Foreign Application Priority Data

Jun. 14, 1979 [NL] Netherlands ............................ 7904651

[51] Int. Cl.³ ........................ C07C 29/86; C07C 45/80
[52] U.S. Cl. ..................................... 568/366; 568/836; 568/835; 568/832
[58] Field of Search ................ 568/338, 366, 836, 832, 568/835

[56] References Cited

U.S. PATENT DOCUMENTS

| 3,179,699 | 4/1965 | Waldmann | 568/836 |
| 3,340,304 | 9/1967 | Schulz et al. | 568/836 |
| 3,391,190 | 7/1968 | Kilsheimer et al. | 568/836 |
| 3,439,041 | 4/1969 | Gey et al. | 568/836 |
| 4,163,027 | 7/1979 | Magnussen et al. | 568/366 |
| 4,283,560 | 8/1981 | Choo et al. | 568/835 |

FOREIGN PATENT DOCUMENTS 7004497 9/1971 Netherlands ........................ 568/836

OTHER PUBLICATIONS

Magnusse et al., Chem. Abst., vol. 89, #214,989f (1978).

Primary Examiner—Nicky Chan
Assistant Examiner—James H. Reames
Attorney, Agent, or Firm—Cushman, Darby & Cushman

[57] ABSTRACT

The invention relates to a method for removal of alkali metal carboxylates from mixtures which contain a cycloalkanone and a cycloalkanol, in particular cyclohexanone and cyclohexanol, and which have been obtained in oxidation in the liquid phase of the corresponding cycloalkane with gas containing molecular oxygen.

According to the invention, alkali metal carboxylates are removed from such mixtures containing a cycloalkanone and a cycloalkanol by washing the mixture with an aqueous acid solution, in particular an aqueous solution of carboxylic acid with 1–6 carbon atoms per molecule.

The invention provides a solution to the problem of the so-called alkali entrainment, which leads to loss of cycloalkanone owing to condensation into undesired high-boiling by-products in the following distillation for gaining pure cycloalkone. This substantial loss is prevented by the method according to the invention.

13 Claims, 1 Drawing Figure

PROCESS FOR REMOVING ALKALI METAL CARBOXYLATES FROM MIXTURES CONTAINING A CYCLOAKANONE AND A CYCLOALKANOL OBTAINED IN OXIDATION OF CYCLOALKANES

The invention relates to a process for removing alkali metal carboxylates from mixtures containing a cycloalkanone and a cycloalkanol and obtained in oxidation of the corresponding cycloalkane in the liquid phase with a gas containing molecular oxygen.

The preparation of mixtures containing a cycloalkanone and a cycloalkanol by oxidation of the corresponding cycloalkane, and in particular a cycloalkane with 5–12 carbon atoms in the ring, in the liquid phase with a gas containing molecular oxygen is well known. (See e.g. the review articles in Stanford Research Institute reports 3 (1965), 3A (1971), 7 (1965), 307–319 and 7A (1968), 87–103.). The degree of conversion applied is usually low, e.g. 1–12% relative to the cycloalkane supplied, so that the reaction mixture obtained contains a large quantity of unconverted cycloalkane. The mixture further contains a usually considerable quantity of the corresponding cycloalkanone and cycloalkanol, and a minor quantity of by-products, including organic acids and cycloalkyl esters. A common method to upgrade the reaction mixture is to treat it with an aqueous alkaline solution, e.g. an aqueous solution of sodium carbonate or sodium hydroxide, to neutralize the acids present and saponify the readily saponifying cycloalkyl esters. In this so-called neutralization step, a two-phase system is obtained from which the aqueous phase containing the majority of the alkali metal carboxylates produced is separated. The aqueous phase is discharged as effluent. The organic phase is upgraded further by distillation, the cycloalkane and the by-products that are more volatile than the cycloalkanone being distilled off first, then the cycloalkanone and finally the cycloalkanol. A high-boiling residue then remains that contains, among other things, high-boiling cycloalkyl esters.

A known method is used to increase the cycloalkanol yield, by saponifying the cycloalkyl esters still remaining in the reaction product after the cycloalkane has been distilled off by treatment with an aqueous alkaline solution, e.g. a sodium hydroxide or sodium carbonate solution. In this so-called saponification step, too, a two-phase system is obtained with an aqueous phase containing the majority of the alkali metal carboxylates produced in this saponification and discharged as effluent, and an organic phase that is further upgraded.

If so required, various modifications can be applied, e.g. pre-washing the reaction mixture with water, before the neutralization step, distilling off the cycloalkane before the neutralization step, distilling off the cycloalkane first after the saponification step, combining the neutralization step and the saponification step or omitting one of the two, etc.

A serious problem of these methods, especially when applying a saponification step after the cycloalkane has been distilled off, is constituted by so-called alkali entrainment. The organic phase of the two-phase system obtained still contains a considerable amount of alkali metal carboxylates. This exhibits a basic character and in the following distillation, especially distillations in which cycloalkanone is present and the bottom temperature in the distillation columm is relatively high, it leads to loss of cycloalkanone by condensation to unwanted high-boiling by-products. The alkali entrainment is due on the one hand to the solubility of the alkali metal carboxylates in the organic phase, which still contains a fair amount of dissolved water, and on the other to incomplete phase separation, which causes very small droplets of aqueous phase containing alkali metal carboxylates to remain emulsified in the organic phase. The water disappears in the later distillations, but the alkali metal carboxylates remain behind in the organic mixture.

Washing the organic phase containing alkali metal carboxylates with water has been found to have little effect. The alkali metal carboxylates can only with extreme difficulty be removed to an adequate extent in this way.

The invention now provides a solution to this problem. According to the invention, alkali metal carboxylates are eliminated from mixtures containing a cycloalkanone and a cycloalkanol and obtained in oxidation of the corresponding cycloalkane in the liquid phase with a gas containing molecular oxygen by washing the mixture with an aqueous acid solution.

The method according to the invention enables alkali metal carboxylates to be effectively removed from the said mixtures, so that alkali entrainment and the accompanying loss of cycloalkanone by condensation to undesirable high-boiling by-products is prevented. Moreover, it is sufficient to use a relatively small quantity of washing liquor, so that there is only a small quantity of spent washing liquor to be purified or otherwise processed as effluent. Finally, fouling of the upgrading apparatus is reduced.

In the method according to the invention, the aqueous acid solution used is preferably a solution of a carboxylic acid with 1–6 carbon atoms per molecule, in particular formic acid, acetic acid, propionic acid, butyric acid and/or caproic acid. It is of advantage to use an aqueous solution obtained as a by-product of the cycloalkane oxidation, e.g. by washing the cycloalkane oxidation reaction mixture with water before this mixture is treated with an alkaline solution. If so required, aqueous solutions of other acids can also be used, e.g. sulphuric acid, phosphoric acid or nitric acid, but this is of no advantage.

The method according to the invention is applicable for mixtures containing a cycloalkanone and a cycloalkanol that are obtained in the said neutralization step and saponification step, with or without the aforementioned modifications, or other treatments in which mixtures containing a cycloalkanone and a cycloalkanol that are obtained by oxidation of a cycloalkane are treated with aqueous alkaline solutiions, e.g. those described in the applicant's non-prepublished Netherlands Patent Application 78 08416. The method according to the invention is of special advantage for processing mixtures obtained in such treatment carried out after removal of unconverted cycloalkane. Henceforth the invention is therefore described with reference to this case, without however being restricted to it.

The cycloalkanone/cycloalkanol preferably has 5–12 carbon atoms in the ring. Examples are cyclopentanone/cyclopentanol, cyclododecanone/cyclodecanol and in particular cyclohexanone/cyclohexanol.

The mixture containing alkali metal carboxylates, cycloalkanone and cycloalkanol which is to be treated may in practice also contain cycloalkane. This may have been left over from the oxidation step, or have been added e.g. as described in British Patent No. 982,647. The alkali metal carboxylate content is say 5 to 100 mgeq/kg.

The alkali metal carboxylates are usually sodium carboxylates, as the alkaline solution with which the cycloalkane oxidation reaction mixture is treated is usually a solution of sodium hydroxide and/or sodium carbonate. The alkali metal carboxylates may also be e.g. potassium salts, however.

The quantity of acid in the aqueous acid solution relative to the mixture to be treated in e.g. 0.05 to 20 mgeq per kg organic mixture, preferably 0.5 to 2.5 mgeq/kg. The acid content of the aqueous solution is e.g. 1 to 200 mgeq per kg aqueous solution, preferably 5 to 50 mgeq/kg.

The reaction temperature in the process according to the invention preferably lies between 30° and 100° C., and more in particular between 60° C. The pressure may lie e.g. between 10 and 1000 kPa, preferably between 50 and 200 kPa. The duration of the treatment may lie e.g. between 5 and 60 minutes.

The reader is referred for further details to the annexed reaction flowsheet. The cycloalkanone is here cyclohexanone, but the method according to the invention is also suitable for preparing other cycloalkanones with 5-12 carbon atoms in the ring, e.g. cyclopentanone or cyclododecanone.

Cyclohexane is fed via line 1 to oxidation reactor 2. Air or another gas containing molecular oxygen is fed via line 3 to reactor 2, where a liquid phase of cyclohexane and oxidation products is maintained. Off-gas escapes through line 4 component; cyclohexane vapour is condensed in a device that is not shown and returned to reactor 2. The liquid reaction mixture, which contains cyclohexanone, cyclohexanol, unconverted cyclohexane, carboxylic acids, esters and other by-products, flows via line 5 to neutralization device 6, e.g. a mixer-settler, where it is washed with an aqueous sodium carbonate solution supplied via line 7. The quantity of sodium carbonate is such that no unconverted base remains in device 6. A vapour phase is discharged via line 8. Cyclohexane is condensed from the vapour phase, and returned to reactor 2. The liquid mixture from neutralization device 6 passes via line 9 to separator 10, where it is separated into an aqueous phase, which is discharged via line 11, and an organic phase, which passes via line 12 to washing device 13. Device 13 may for example be an extraction column or a mixer-settler. The organic phase containing sodium carboxylates is here washed with an aqueous acid solution, in this case an aqueous acetic acid solution, which is supplied via line 14. The aqueous extract phase is discharged via line 15, while the organic extracted phase, which is now substantially free of sodium carboxylates, is fed via line 16 to distillation column 17, where the unconverted cyclohexane is distilled off. The vapour is discharged via line 18, condensed and returned to reactor 2. It is also possible to feed the organic phase from separator 10 direct to distillation column 17. The distillation residue from distillation column 17, which consists substantially of cyclohexanone and cyclohexanol and also contains esters and other contaminants, passes via line 19 to ester saponification vessel 20, to which an aqueous sodium hydroxide solution is fed via line 21. Here cyclohexyl carboxylates are saponified by a known method, with an additional quantity of cyclohexanol being formed in addition to sodium carboxylates. The reaction mixture from the ester saponification passes via line 22/23 to separator 24. If so required, cyclohexane can be added to separartor 24 via line 25 to enhance phase separation, e.g. 10–100 parts by weight, preferably 20–40 parts by weight per 100 parts by weight organic phase. In separator 24 the mixture is separated into an aqueous phase, which is discharged via line 26 and can for example be added to line 7 as a substitute for sodium carbonate in the neutralization step, and an organic phase, which passes via line 27 to washing device 28. This washing device may again be an extraction column or a mixer-settler. The organic phase containing sodium carboxylates is here washed with an aqueous acid solution, in this case an aqueous acetic acid solution, which is supplied via line 29. The aqueous extract phase is fed via line 30 and line 23 to separator 24 and leaves the system together with the aqueous phase of the saponification step via line 26, while the washed organic mixture, which is now substantially free of sodium carboxylates, is fed via line 31 to distillation column 32. In column 32 a fraction boiling lower than cyclohexanone (e.g. pentanol or heptanone) is distilled off. The light fraction is discharged via line 33, while the heavier fraction passes via line 34 to a second distillation column 35. The cyclohexanone is here distilled off and recovered via line 36. The heavier fraction passes via line 37 to a third distillation column 38. Cyclohexanol is distilled off and if so required fed via line 39 to a dehydrogenation unit that is not shown, where it can be converted by dehydrogenation by a known method to an additional quantity of cyclohexanone. The dehydrogenation product can be returned via a line that is not shown to the distillation unit. A distillation residue containing by-products leaves the system via line 40.

The invention is further elucidated with the following numerical examples and comparative experiments.

EXAMPLES AND COMPARATIVE EXPERIMENTS

Example I

A mixture of cyclohexanone, cyclohexanol, cyclohexane, sodium carboxylates and other by-products, obtained by oxidation of cyclohexane in the liquid phase with a gas containing molecular oxygen, elimination of the acid by-products, evaporation of the unconverted cyclohexane, saponification of esters present by means of an aqueous sodium hydroxide solution, addition of 40 wt. % (relative to the organic phase) cyclohexane and separation of the aqueous phase (flow in line 27 of the diagram), is washed in a separating funnel with 12 wt. % water. The washed mixture still contains 25 ppm by wt. sodium in the form of sodium carboxylates. This mixtures is then washed again with 10 vol. % of an aqueous acetic acid solution containing 10 mgeq/kg acetic acid. The sodium carboxylate content of the organic phase has dropped to 0.4 ppm by wt., calculated as sodium. Clarification of the organic phase shows that complete phase separation is achieved.

Example II

Example I is repeated, but using an aqueous acetic acid solution containing 50 mgeq/kg acetic acid. The sodium carboxylate content of the organic phase has now dropped to 0.2 ppm by wt., calculated as sodium.

Comparative Experiment A

Example I is repeated, but using pure water instead of an aqueous acetic acid solution. The sodium carboxylate content of the organic phase is now 2.8 ppm by wt., calculated as sodium. The organic phase remains cloudy, showing that phase separation is incomplete.

Example III

The flow in line 27 of the FIGURE, obtained as described in Example I, is extracted at 60° C. in a continuous process in a mixer-settler with an aqueous acetic acid solution. The throughput of the organic feed is 4.50 l/h, that of the aqueous acid solution 0.54 l/h. The acetic acid content of the aqueous solution is 50 mgeq/kg. The sodium content of the feed is 570 ppm by wt. After the extraction the extracted organic liquid contains only 15 ppm sodium.

Example IV

Example III is repeated with an organic feed containing 122 ppm sodium in the form of sodium carboxylates and an aqueous solution containing 25 mgeq/kg acetic acid. The throughput of the organic feed is 15.00 l/h, that of the aqueous acetic acid solution 3.00 l/h. After the extraction the extracted organic liquid contains only 5 ppm sodium.

Comparative Experiment B

Example III is repeated, but using pure water instead of the aqueous acetic acid solution. After the extraction the organic phase contains 149 ppm sodium in the form of sodium carboxylates.

I claim:

1. A process for the purification of organic solution mixtures of a cycloalkanone and a cycloalkanol in the corresponding cycloalkane, and containing a minor quantity of by-product impurities including organic acids and cycloalkyl esters, produced from the molecular oxygen oxidation of said corresponding cycloalkane, which comprises the combination of steps of
    (1) treating said organic solution mixture with an aqueous alkaline solution to neutralize and/or saponify said acids and esters, whereby a two-phase organic/aqueous liquid system is formed, and separating an organic phase therefrom containing said cycloalkanone and cycloalkanol now contaminated with alkali metal organic carboxylic acid salts; and then
    (2) washing said cycloalkanone/cycloalkanol components of said organic phase with an aqueous acid solution, containing from 0.05 to 20 mgeq/kg relative to the organic mixture, whereby a second two-phase organic/aqueous liquid system is formed; and
    (3) separating the organic phase of said second two-phase system from the aqueous acid phase, to obtain a cycloalkanone/cycloalkanol product now substantially free from (a) organic acids and cycloalkyl esters and (b) alkali metal acid salts.

2. The process of claim 1, wherein said aqueous acid solution contains an organic carboxylic acid or a strong mineral acid.

3. The process of claim 2, wherein said acid is a carboxylic acid of the group consisting of formic acid, acetic acid, proprionic acid, butyric acid and caproic acid.

4. The process of claim 2, wherein said acid is a strong mineral acid.

5. The process of claim 1 or claim 2, wherein said aqueous acid solution contains from 1 to 200 mgeq/kg of acid.

6. The process of claim 1 or claim 2, wherein said aqueous acid solution contains from 5 to 50 mgeq/kg of acid.

7. The process of claim 1 or 2, wherein the quantity of acid employed in said aqueous acid solution, relative to the said mixture being treated is from 0.5 to 2.5 mgeq/kg of said mixture.

8. The process of claim 1 or claim 2, wherein said cycloalkanone and said cycloalkanol each has from 5 to 12 carbon atoms in the ring.

9. The process of claim 1 or claim 2, wherein said cycloalkanone is cyclohexanone and said cycloalkanol is cyclohexanol.

10. The process of claim 1 or claim 2, wherein said process is conducted at a temperature between 30° and 100° C.

11. The process of claim 1 or claim 2, wherein said process is conducted at a temperature between 60° and 95° C.

12. The process of claim 1 or claim 2, wherein prior to said treating step (1), said cycloalkane is first removed therefrom.

13. The process of claim 1 or claim 2, wherein prior to said treating step (1), said solution mixture is first washed with water.

* * * * *